US008975309B2

(12) United States Patent
Stromme et al.

(10) Patent No.: US 8,975,309 B2
(45) Date of Patent: Mar. 10, 2015

(54) VINYL ALCOHOL CO-POLYMER CRYOGELS, VINYL ALCOHOL CO-POLYMERS, AND METHODS AND PRODUCTS THEREOF

(76) Inventors: Maria Stromme, Uppsala (SE); Albert Mihranyan, Uppsala (SE)

( * ) Notice: Subject to any disclaimer, the term of this patent is extended or adjusted under 35 U.S.C. 154(b) by 377 days.

(21) Appl. No.: 12/998,077

(22) PCT Filed: Sep. 14, 2009

(86) PCT No.: PCT/IB2009/054012
§ 371 (c)(1),
(2), (4) Date: Jun. 2, 2011

(87) PCT Pub. No.: WO2010/029517
PCT Pub. Date: Mar. 18, 2010

(65) Prior Publication Data
US 2011/0230567 A1    Sep. 22, 2011

Related U.S. Application Data

(60) Provisional application No. 61/096,976, filed on Sep. 15, 2008.

(51) Int. Cl.
```
A61F 2/00       (2006.01)
C08F 220/12     (2006.01)
C08F 220/18     (2006.01)
C08F 16/06      (2006.01)
A61K 9/00       (2006.01)
C08F 218/08     (2006.01)
A61K 47/34      (2006.01)
A61L 27/52      (2006.01)
A61K 9/06       (2006.01)
A61L 27/16      (2006.01)
A61K 9/19       (2006.01)
A61K 9/70       (2006.01)
C08J 5/18       (2006.01)
C08F 220/06     (2006.01)
C08F 220/56     (2006.01)
```

(52) U.S. Cl.
CPC ............... *A61L 27/16* (2013.01); *A61K 9/006* (2013.01); *C08F 218/08* (2013.01); *A61K 47/34* (2013.01); *A61K 9/0024* (2013.01); *A61K 9/0065* (2013.01); *A61K 9/0014* (2013.01); *A61L 27/52* (2013.01); *A61K 9/06* (2013.01); *C08F 220/06* (2013.01); *A61K 9/19* (2013.01); *C08F 220/56* (2013.01); *A61K 9/0031* (2013.01); *A61K 9/7007* (2013.01); *C08J 5/18* (2013.01)
USPC .............. 523/113; 524/831; 524/833; 525/60

(58) Field of Classification Search
USPC ...................... 523/113; 524/831, 833; 525/60
See application file for complete search history.

(56) References Cited

U.S. PATENT DOCUMENTS

2003/0153708 A1    8/2003    Caneba et al.
2005/0250919 A1    11/2005   Caneba et al.

FOREIGN PATENT DOCUMENTS

| EP | 0058794 | 8/1982 |
|---|---|---|
| EP | 0058497 | 8/1985 |
| GB | 835651 | 5/1960 |
| JP | 47-012854 | 1/1972 |
| JP | 52-027455 | 3/1977 |
| JP | 57-130543 | 8/1982 |
| JP | 2001-81128 A | 3/2001 |
| RU | 2252945 | 5/2005 |
| WO | WO 98/50017 | 11/1998 |
| WO | WO2004/092264 | 10/2004 |
| WO | WO 2006/119968 | 11/2006 |
| WO | WO2007/092631 | 8/2007 |

OTHER PUBLICATIONS

Saxena SK. Polyvinyl Alcohol (PVA). Chemical and Technical Assessment. 61st JECFA, 2004.*
Barbani et al., Hydrogels based on poly(vinyl alcohol-co-acrylic acid) as an innovative system for controlled drug . . . , Journ of Appl Biomaterials & Biomechanics 2004: 2:192.
Ma et al., Synthesis and properties of physically crosslinked poly (vinyl alcohol) hydrogels, Jounal of China U of Mining and Technology, 18, (2008), 271-274.
Barbani et al., Bioartificiai materials based on blends of dextran and poly(vinyl alcohol-co-acrylic acid), Eruopean Polymer Journal, 41 (2005), 3004-3010.

(Continued)

*Primary Examiner* — Paul Zarek
(74) *Attorney, Agent, or Firm* — Ryan Kromholz & Manion, S.C.

(57) ABSTRACT

A cryogel-forming vinyl alcohol co-polymer is operable to form a cryogel, i.e., a hydrogel formed by crytropic gelation, in an aqueous solution at a concentration of less than about 10% by weight, in the absence of a chemical cross-linking agent and in the absence of an emulsifier. In one embodiment, a vinyl alcohol co-polymer cryogel comprises at least about 75% by weight water and a vinyl alcohol co-polymer, wherein the vinyl alcohol co-polymer is operable to form a cryogel in an aqueous solution at a concentration of less than about 10% by weight, in the absence of a chemical cross-linking agent and in the absence of an emulsifier. In another embodiment, a vinyl alcohol co-polymer cryogel comprises at least about 75% by weight water and a vinyl alcohol co-polymer comprising a saponified product of a vinyl acetate co-polymer formed from at least about 80% by weight of vinyl acetate monomer, and (i) at least about 3% by weight of acrylamide monomer or a mixture of acrylamide monomer and acrylic acid monomer, or (ii) at least about 5% by weight acrylic acid monomer. The vinyl acetate co-polymer, vinyl alcohol co-polymer and vinyl alcohol co-polymer cryogel may be formed according to particular methods, and the vinyl alcohol co-polymer cryogels may be used in various applications including biomedical implants and thin films and for delivery of therapeutic or cosmetic agents.

37 Claims, 7 Drawing Sheets

(56) References Cited

OTHER PUBLICATIONS

Ranjha et al., pH-Sensitive Noncrosslinked Poly (vinyl alcohol-co-acrylic acid) Hydrogels for Site Specific Drug Delivery, Saudi Pharmaceutical Journal, 7, 137-143 (1999).

Hirari et al., Ph-iInduced Structure Change of poly(vinyl alcohol) Hydrogel, Crosslinked with Poly (acrylic acid), Angewandte Makromolekulare Chemie, 240, 213-219 (1996).

Coluccio et al., Preparation and characterization of poly (vinyl alcohol-co-Acrylic acid) microparticles . . . , J of Appl Biomaterials and Biomechanics, 2, 202 (2004).

Canal et al., Correlation between mesh size and equilibrium degree of swelling of polymeric networks, Journal of Biomedical Materials Research, 23, 1183-1193 (1989).

Kurihara et al., Crosslinking of poly (vinyl alcohol)-graft-N-isopropylacrylamide copolymer membranes . . . , Polymer, 37, 1123-1128 (1996).

McKenna et al., Effect of crosslinks on the thermodynamics of poly (vinyl alcohol) hydrogels, Polymer, 35, 5737-5742 (1994).

Stauffer et al., Poly(vinyl alcohol) hydrogels preprared by freezing-thawing cyclic processing, Polymer, 33, 3932-3936, (1992).

Urushizaki et al., Swelling and mechanical properties of poly (vinyl alcohol) hydrogels., International Journal of Pharmaceutics, 58, 135-142 (1990).

Peppas et al, Controlled release from poly (vinyl alcohol) gels prepared by freezing-thawing process, Journal of Controlled Release, 18, 95-100 (1992).

Pinther et al., Polymere Hydrogele als Wirkstoffmatrices, Jena Matn. Nat. Wiss. Reihe, 36, 669(1987). english abstract.

Yoshi et al., Heat Resistance Poly (vinyl alcohol) Hydrogel, Radiation Physics and Chemistry, 46, 169-174 (1995).

Nambu, Rubber-Like Poly (vinyl alcohol) Gel, Kobunshi Ronbunshu, 47, 695-703 (1990). english abstract.

Peppas et al., Reinforced uncrosslinked poly (vinyl alcohol) gels produced by cyclic freezing-thawing processes: a short review, J of Controlled Release, 16, 305-310 (1991).

Lozinsky et al., Cryotropic Gelation of Poly (vinyl alcohol) Solutions, Uspekhi Khimii, 67, 641-655 (1998) english abstract.

Hernandez et al., Viscoelastic properties of poly (vinyl alcohol) hydrogels and ferrogels obtained through freezing-thawing cycles, Polymer, 45, 5543-5549 (2004).

Domotenko et al., Influence of Regimes of Freezing of Aqueus Solutions of Polyvinyl Alchohol . . . , Vysokomolekulyarnye Soedineniya Seriya, A30, 1661-1666 (1988) Eng abstract.

Yokoyama et al., Morphology and structure of highly elastic poly-(vinyl alcohol) hydrogel prepared by repeated freezing and melting, Coll. Polym. Sci., 264, 595-601 (1986).

Watase et al., Rheological and DSC Changes in Poly (vinyl alcohol) Gels induced by immersion in water, Journal of Polymer Sci Part B—Polmer Physics, 23; 1803-1811 (1985).

Lozinsky et al, Poly(vinyl alcohol) cryogels employed as matrices for cell immobilization . . . , Enzyme and Microbial Technology, 23, 227-242, (1998).

Takigawa et al., Swelling and mechanical properties of polyvinylalcohol hydrogels, Polymer Bulletin, 24, 613-618 (1990).

Barbani et al., Hydrogels based on poly(vinly alcohol-co-acrylic acid) . . . Journal of Applied Biomaterials & Biomechanics, vol. 2, 2004 p. 192.

Ru-Yin et al., "Synthesis and properties of physically crosslinked poly . . . "; Journal of China University of Minint and Technology; vol. 18, No. 2; Jun. 1, 2008, pp. 271-274.

Barbani et al; "Bioartificial materials based on blends of dextran and poly . . . "; European Polymer Journal Pergamon Press, vol. 41, No. 12, Dec. 1, 2005, pp. 3004-3010.

International Preliminary Report on Patentability for PCT/IB2009/054012 dated Mar. 24, 2011.

\* cited by examiner

VINYL ALCOHOL CO-POLYMER CRYOGELS, VINYL ALCOHOL CO-POLYMERS, AND METHODS AND PRODUCTS THEREOF

FIELD OF THE INVENTION

The present invention is directed to vinyl alcohol co-polymer cryogels, i.e., hydrogels formed by cryotropic gelation, vinyl alcohol co-polymers suitable for forming the cryogels, and vinyl acetate co-polymers suitable for forming the vinyl alcohol co-polymers. The present invention is also directed to methods of forming vinyl acetate co-polymers, methods of forming vinyl alcohol co-polymers, and methods of forming vinyl alcohol co-polymer cryogels. In further embodiments, the invention is directed to biomedical implants and thin films formed from the vinyl alcohol co-polymer cryogels and to delivery systems for therapeutic or cosmetic agents.

BACKGROUND OF THE INVENTION

Conventional polyvinyl alcohol (PVA) is a widely used polymer in fibers, adhesives, films, membranes, fishing baits, and drug delivery vehicles. PVA is also commonly used as a base for various pharmaceutical and non-pharmaceutical chewing gums. Co-polymers of PVA with acrylic or methacrylic acid have been studied for controlled drug delivery and for pH-sensitive smart drug delivery vehicles (Ranjha et al, "pH-sensitive non-crosslinked poly(vinyl alcohol-co-acrylic acid) hydrogels for site specific drug delivery," *Saudi Pharmaceutical Journal*, 7(3):137-143 (1999); Hirai et al, "pH-Induced structure change of poly(vinyl alcohol) hydrogel crosslinked with poly(acrylic acid)," *Angewandte Makromolekulare Chemie*, 240:213-219 (1996); Barbani et al, "Hydrogels based on poly(vinyl alcohol-co-acrylic acid) as innovative system for controlled drug delivery," *Journal of Applied Biomaterials and Biomechanics*, 2:192 (2004); and Coluccio et al, "Preparation and characterization of poly(vinyl alcohol-co-acrylic acid) microparticles as a smart drug delivery system," *Journal of Applied Biomaterials and Biomechanics*, 2:202 (2004)).

Conventional PVA hydrogels have also been extensively studied for biomedical applications, for example, in soft tissue applications wherein their high water content and rheology are well suited. Crosslinking has been studied as a mechanism for controlling the mechanical properties of PVA, including cross-linking by addition of chemical agents, e.g. glutaraldehyde (Canal et al, "Correlation between Mesh Size and Equilibrium Degree of Swelling of Polymeric Networks," *Journal of Biomedical Materials Research*, 23:1183-1193 (1989); Kurihara et al, "Crosslinking of poly(vinyl alcohol)-graft-N-isopropylacrylamide copolymer membranes with glutaraldehyde and permeation of solutes through the membranes," *Polymer*, 37:1123-1128 (1996); and Mckenna, et al, "Effect of Cross-Links on the Thermodynamics of Poly (Vinyl Alcohol) Hydrogels," *Polymer*, 35:5737-5742 (1994)), crosslinking by irradiation/photopolymerisation, and crosslinking by cryotropic gelation (Stauffer et al, "Poly(Vinyl Alcohol) Hydrogels Prepared by Freezing-Thawing Cyclic Processing," *Polymer*, 33:3932-3936 (1992); Urushizaki et al, "Swelling and Mechanical-Properties of Poly(Vinyl Alcohol) Hydrogels," *International Journal of Pharmaceutics*, 58:135-142 (1990); and Peppas et al, "Controlled Release from Poly(Vinyl Alcohol) Gels Prepared by Freezing-Thawing Processes," *Journal of Controlled Release*, 18:95-100 (1992)).

However, glutaraldehyde is known to be toxic to cells; accordingly, hydrogels prepared with such chemical crosslinking agents have limited applications unless the absence of unreacted toxic entities is reassured. Irradiation-crosslinked PVA hydrogels have been described for controlled release of biologically active substances (Penther et al, *Jena Math. Nat. Wiss. Reihe*, 36:669 (1987)). However, these gels are generally weak (Yoshii et al, *Radiation Physics and Chemistry*, 46:169-174 (1995)), and the irradiation methods are typically expensive and difficult for industrial scale-up.

Cryotropic gelation, i.e., gel formation upon consecutive freezing, for example in a temperature range between −5 and −196° C., and thawing, is a physical method of gel formation which is suited best for pharmaceutical and biotechnological applications as it avoids use of potentially hazardous crosslinking agents or irradiation to manufacture firm hydrogels. Such cryogels can act as drug delivery vehicles useful in, e.g., controlled release formulations. Early cryogels were made in the 1940s in Germany where sponges were produced by freezing of starch paste. Cryogels from PVA solutions were described in the 1970s for manufacturing jelly fish baits (Inoue et al, "Water-resistant poly(vinyl alcohol) plastics," Japanese Patent No. 47-012854 (1972)). Descriptions of cryogelling properties of polyvinyl alcohol polymers are provided by Nambu, "Rubber-like poly(vinyl alcohol) gel," *Kobunshi Ronbunshu*, 47:695-703 (1990); Peppas et al, "Reinforced Uncrosslinked Poly (Vinyl Alcohol) Gels Produced by Cyclic Freezing-Thawing Processes—a Short Review," *Journal of Controlled Release*, 16:305-310 (1991); and Lozinsky, "Cryotropic gelation of poly(vinyl alcohol) solutions," *Uspekhi Khimii*, 67:641-655 (1998). PVA-based hydrogel systems have been used to develop various stimuli-responsive pharmaceutical systems which undergo significant volume transitions with relatively small changes in the environmental conditions, e.g. pH, magnetic field, or light (Hernandez et al, "Viscoelastic properties of poly(vinyl alcohol) hydrogels and ferrogels obtained through freezing-thawing cycles," *Polymer*, 45(16):5543-5549 (2004)).

PVA is probably the most common polymer among cryogelling agents for biomedical applications because it is non-toxic and biocompatible. Further, the structure-functionality relationship of PVA-based cryogels has been extensively described. Generally, PVA gels with larger molecular mass form firmer cryogels than analogues with lower molecular mass (Lozinsky, supra). This is because polymer chain elongation increases the possibility of entanglement between adjacent chains and eventually local crystallization. However, high molecular mass polymers are known to have lower solubility. Similarly, higher density of available side chains produces firmer gels than analogues with lower degrees of branching (Id.).

The mechanism of cryogel formation is complex. In brief, it is believed that during freezing, local areas of high polymer concentration are formed and promote crystallite formation and cross-linking between polymer chains resulting in a macroporous mesh (Domotenko et al, "Influence of Regimes of Freezing of Aqueous Solutions of Polyvinyl-Alcohol and Conditions of Defreezing of Samples on Properties of Obtained Cryogels," *Vysokomolekulyarnye Soedineniya Seriya, A* 30:1661-1666 (1988)). As a result, PVA chains form the ordered structures known as microcrystallinity zones (Yakoyama et al, "Morphology and structure of highly elastic poly(vinyl alcohol) hydrogel prepared by repeated freezing-and-melting," *Coll. Polym. Sci.*, 264:595-601 (1986)). They act as junction knots which in turn arise only when the OH groups are free to participate in interchain interactions. Inasmuch as an industrial PVA is commonly manufactured by the saponification of poly(vinyl acetate), the degree of deacetylation along with the polymer molecular weight and tacticity are crucial in determining the ability of PVA solutions to gel and particularly to gel via cryotropic gelation, since the residual acetyl groups will interfere with the coupling of the sufficiently long intermolecular contacts needed for the formation of PVA crystallites. Therefore, for the preparation of rigid cryogels of PVA, it is necessary to use highly-deacetylated PVA (Watase et al, "Rheological and DSC Changes in Polyvinyl-Alcohol) Gels Induced by Immersion in Water," *Journal of Polymer Science Part B-Polymer Physics*, 23:1803-1811 (1985)).

While hydrogels in general can have a range of mechanical properties depending on their chemistry and water content, they generally have a relatively low mechanical strength (*Hydrogels in Medicine and Pharmacy: Vol. I-III*, Peppas, Ed., CRC Press Boca Raton, Fla. (1986). Currently known PVA-based cryogels typically form firm gel structures at concentrations around 14-16% by wt (Lozinsky, supra) and additional cross-linking agents may often be used. Concentrated PVA solutions are typically used for the preparation of mechanically rigid cryogel matrices; however, very concentrated (>20% by wt) solutions of PVA are excessively viscous, especially when the polymer molecular weight exceeds 60-70 kDa. (Lozinsky et al, "Poly(vinyl alcohol) cryogels employed as matrices for cell immobilization. 3. Overview of recent research and developments," *Enzyme and Microbial Technology*, 23:227-242 (1998)). The Lozinsky Russian Patent No. 2003-131705/04 discloses that PVA-based cryogels are formed at concentrations between 3-25% by wt with the addition of a surface active agent and that the addition of surface active agents (herein and elsewhere also referred to as emulsifiers) was found crucial for obtaining both physical crosslinking between adjacent polymer chains and high macro-porosity. The Lozinsky patent further discloses that the chemical character of the emulsifier (cationic, anionic, or amphoteric) is not critical as long as it was present in the composition.

As noted, PVA is typically manufactured by the saponification of poly(vinyl acetate). A commonly used polymerization route of polyvinyl-acetate-based polymers utilizes emulsifiers or protective hydrocolloids for successful polymerization. Further, organic solvents are conventionally used in the process (i.e. the so-called varnish method), which are hazardous and environmentally unfriendly and therefore require special handling. In addition, during saponification of vinyl acetate products, a hard jelly-like mass is conventionally formed and is then broken using high-shear homogenizers, requiring a significant input of energy. GB Patent No. 835,651 discloses a vinyl acetate polymer prepared with a limited amount of acrylamide to form a stable dispersion that yields a hard water-resistant film on drying at a high temperature.

In view of the non-toxic and biocompatible nature of PVA, further improvements in PVA hydrogels are desirable to allow expanded use of PVA in various applications.

SUMMARY OF THE INVENTION

It is therefore an object of the present invention to provide improved vinyl alcohol-based hydrogels, and more specifically, improved vinyl alcohol-based cryogels, i.e., hydrogels formed by cryotropic gelation. It is a related object to provide materials and methods facilitating such vinyl alcohol-based cryogels, and to provide applications for such vinyl alcohol-based cryogels.

In one embodiment, the present invention is directed to a cryogel-forming vinyl alcohol co-polymer operable to form a cryogel in an aqueous solution at a concentration of less than about 10% by weight, in the absence of a chemical cross-linking agent and in the absence of an emulsifier.

In another embodiment, the invention is directed to a method of forming vinyl acetate co-polymer, the method comprising copolymerizing at least about 80% by weight of vinyl acetate monomer, and either (i) at least about 3% by weight of acrylamide monomer or a mixture of acrylamide monomer and acrylic acid monomer, or (ii) at least about 5% by weight acrylic acid monomer, based on the weight of the monomers, in an aqueous medium with a polymerization initiator and a buffer, wherein the aqueous medium is free of emulsifier. The resulting vinyl acetate co-polymer may be used, inter alia, in forming a vinyl alcohol co-polymer. Thus, in a related embodiment, the invention is directed to a method of forming a cryogel-forming vinyl alcohol co-polymer, comprising forming a vinyl acetate co-polymer according to the aforementioned method, and saponifying the vinyl acetate co-polymer to form the cryogel-forming vinyl alcohol co-polymer.

In another embodiment, the invention is directed to a method of forming a vinyl alcohol co-polymer cryogel. The method comprises freezing an aqueous solution of the vinyl alcohol co-polymer of the invention at a temperature of from 0° C. to about −196° C. to form a molded mass, and thawing the molded mass to form a hydrogel.

In further embodiments, the invention is directed to vinyl alcohol co-polymer cryogels. In one embodiment, a vinyl alcohol co-polymer cryogel comprises at least about 75% by weight water and is formed from a vinyl alcohol co-polymer operable to form a cryogel in an aqueous solution at a concentration of less than about 10% by weight, in the absence of a chemical cross-linking agent and in the absence of an emulsifier. In another embodiment, a vinyl alcohol co-polymer cryogel comprises at least about 75% by weight water and is formed from a vinyl alcohol co-polymer comprising a saponified product of a vinyl acetate co-polymer formed from at least about 80% by weight of vinyl acetate monomer, and either (i) at least about 3% by weight of acrylamide monomer or a mixture of acrylamide monomer and acrylic acid monomer, or (ii) at least about 5% by weight acrylic acid monomer.

The vinyl alcohol co-polymer cryogels and vinyl alcohol co-polymers of the present invention are advantageous in that they can be readily prepared without emulsifiers and chemical crosslinking agents, and therefore are suitable for use in a wide variety of applications, including topical and in vivo use. Additionally, the vinyl alcohol co-polymer cryogels can advantageously be formed from relatively low concentrations of the vinyl alcohol co-polymer. Properties of the vinyl alcohol co-polymer cryogels can be controlled via, inter alia, the vinyl acetate co-polymers and vinyl alcohol co-polymers employed in the cryogel formation. The methods of the present invention facilitate preparation of the vinyl alcohol co-polymer cryogels and vinyl alcohol co-polymers with desirable characteristics. These and additional objects and advantages are more fully apparent in view of the detailed description which follows.

BRIEF DESCRIPTION OF THE DRAWINGS

The detailed description will be more fully understood in view of the drawings, in which.

Figure 1A:
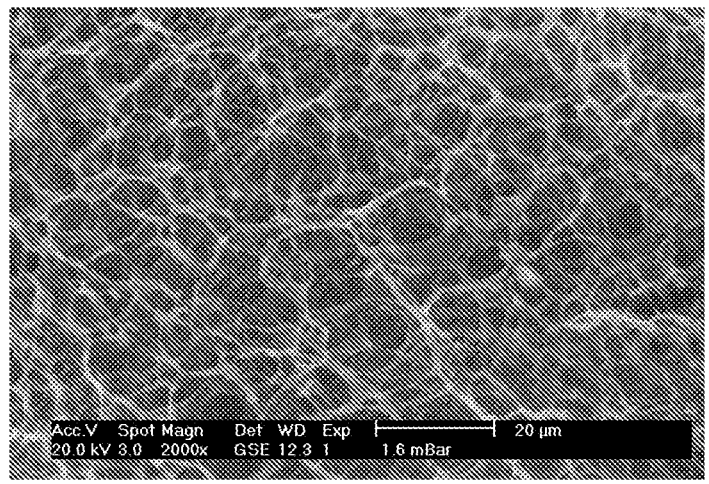
FIGS. 1A-1C show environmental scanning electron microscope (ESEM) pictures of cryogels of Examples 1-3.

The embodiments to which the drawings relate are described in further detail in the Examples. These embodiments are illustrative in nature and are not intended to be limiting of the invention. Moreover, individual features of the drawing and the invention will be more fully apparent and understood in view of the detailed description.

DETAILED DESCRIPTION

The present invention is directed to vinyl alcohol co-polymers and vinyl alcohol co-polymer cryogels, methods of forming vinyl alcohol co-polymers, vinyl acetate co-polymers from which vinyl alcohol co-polymers can be formed, and vinyl alcohol co-polymer cryogels. As will be described in detail herein, the vinyl alcohol co-polymers are suitable for use in a wide variety of applications.

More specifically, the vinyl alcohol co-polymers according to the invention are cryogel-forming vinyl alcohol co-polymers, i.e., they form cryogels upon freezing and thawing, and are operable to form a cryogel in an aqueous solution at a concentration of less than about 10% by weight, in the absence of a chemical cross-linking agent and in the absence of an emulsifier. In more specific embodiments, the vinyl alcohol co-polymers are operable to form a cryogel in an aqueous solution at a concentration of less than about 5% by weight, and in further embodiments, are operable to form a cryogel in an aqueous solution at a concentration of about 1-2% by weight. As conventional vinyl alcohol co-polymers typically are not cryogel-forming in concentrations less than about 14-16% by weight, and often require crosslinkers to form gels having sufficient mechanical strength, the vinyl alcohol co-polymers of the present invention provide a significant advantage over the prior art.

In one embodiment, the vinyl alcohol co-polymer comprises a saponified product of a specific vinyl acetate co-polymer. More particularly, the vinyl acetate co-polymer is formed from at least about 80% by weight of vinyl acetate monomer, and either (i) at least about 3% by weight of acrylamide monomer or a mixture of acrylamide monomer and acrylic acid monomer, or (ii) at least about 5% by weight acrylic acid monomer. Within the present disclosure, "acrylic acid monomer" is inclusive of acrylic acid and homologs thereof, including, but not limited to methyl, ethyl and propyl acrylic acids and acrylates, and "acrylamide monomer" is inclusive of acrylamide and homologs thereof, including, but not limited to methyl, ethyl and propyl acrylamides. The copolymerization is preferably conducted in the absence of an emulsifier and in an aqueous medium. Within the present disclosure the term "emulsifier" is inclusive of any emulsifier, surface active agent, or surfactant. The acrylamide and/or acrylic acid monomers serve multiple purposes, including a) obtaining a self-emulsifying system, thereby avoiding contaminating emulsifiers, b) facilitating crosslinking during hydrogel formation and controlling hydrogel strength, thereby avoiding contaminating chemical crosslinking agents in hydrogel formation, and/or c) introducing functional groups for pronounced environment-responsive behavior, e.g. pH responsive gels, thermoresponsive gels, and the like. For instance, introducing acrylic acid or acrylamide monomers having ionizable groups of weak acids or bases allows the formation of pH-responsive systems, whereas introducing hydrophobic side chains allows the formation of thermoresponsive gels. Acrylic acid monomer acts primarily as a self-emulsifying agent and facilitates cross-linking during the cryogel formation. Co-polymers containing an acrylamide monomer generally result in firmer cryogels than co-polymers containing solely acrylic acid as the co-monomer. It should be noted that acrylamide monomer-based units are partly hydrolyzed into acrylic acid during the saponification stage in forming the vinyl alcohol co-polymer.

The amount of acrylic acid monomer should not exceed about 20% by wt, more specifically should not exceed about 15% by wt, and even more specifically should not exceed about 10% by wt. Addition of excessive amounts of acrylic acid monomer results in formation of mucilage during the saponification stage and a powdery vinyl alcohol co-polymer product is not obtained. Similarly, the amount of acrylamide monomer should not exceed about 20% by wt, more specifically should not exceed about 15% by wt, and even more specifically not exceed about 10% by wt. Accordingly, the amount of vinyl acetate monomer should be in a range of about 80 to 95% by wt, or about 80 to 97% by wt, or, in more specific embodiments, at least about 85% by wt or in a range of from about 85 to 95% by wt.

The vinyl acetate copolymerization is, in one embodiment, conducted with a polymerization initiator and a buffer. The choice of the initiator for polymerization and its solubility can effect the product properties. The initiator may be water-soluble, e.g., ammonium persulfate or an alkali persulfate such as potassium persulfate, or oil-soluble, e.g., benzoyl peroxide, or a combination thereof. The combination of the two may further influence the functionality of the resultant polymer. Even if the ratios of the original monomers are the same, depending on the choice of the initiator or the combination thereof, polymers are produced with different molecular weights, intrinsic viscosities, and degrees of polydispersity. Suitable buffers include, but are not limited to, bicarbonates, phosphates, and the like.

The vinyl alcohol co-polymer is formed as the saponified product of the vinyl acetate co-polymer. Saponification of the stable vinyl acetate co-polymer emulsion is conducted in alkali medium. Advantageously, the saponification results in the formation of a powdery product, without the formation of hard gel mass which is typically formed in conventional processes. The present method therefore avoids subsequent use of high shear homogenizers for dispersion of a hard gel mass. In one embodiment, the degree of saponification of the resultant product is at least about 90%. In further embodiments, the degree of saponification of the resultant product is above 92%, more specifically above 93%, and even more specifically above 95%. The resultant product consists of a vinyl alcohol co-polymer (PVA) backbone polymer functionalized with acrylic acid, its homologues, acrylamide, its homologues, or combinations thereof. The characteristic viscosities [η] of the obtained PVA products in 0.05M $NaNO_3$ are typically between 1 and 4. The molecular weight of the PVA products is typically between 10,000 and 170,000 Daltons. The polymer product emulsion is characterized by a pH typically of from 3.8 to 5.2 and a dry solid content typically of 30-50% by wt. These numerical ranges are only exemplary of specific, selected embodiments and should not be regarded in a limiting sense.

The vinyl alcohol co-polymer may thus be used to form a vinyl alcohol co-polymer cryogel by freezing an aqueous solution of the vinyl alcohol co-polymer at a temperature in a range of from 0 to about −196° C., more specifically in a range of from about −15 to about −35° C., to form a molded mass, and consecutively thawing the molded mass above freezing temperatures to form the hydrogel. The freezing may be conducted for any suitable time period as desired, for example, from several minutes, e.g., 2, 3, 5, 10, 20, 30, 40 or 50 minutes, up to one or several or more hours, i.e., 2, 3, 5, 10, 15, 20, 24, or 30 hours, or more. Repetitive freeze-thawing for varying times, for example from several minutes up to several hours, may be employed to enhance the gel strength. The cryogels contain more than about 75% by wt water. In specific embodiments, the cryogels contain at least about 90% by wt water and from about 1 to about 10% by weight of the vinyl alcohol co-polymer, more specifically at least about 95% by wt water and from about 1 to about 5% by weight of the vinyl alcohol co-polymer, and in some applications, more than about 96% by wt water and from about 1 to about 4% by weight of the vinyl alcohol co-polymer. The lower threshold concentration of vinyl alcohol co-polymer for cryogel formation is typically around 1% by wt. In a specific embodiment, the vinyl alcohol co-polymer concentration is about 3-4% by wt. Should it be necessary, for example when using the invention to make firm biomedical implants, higher concentrations of the vinyl alcohol co-polymer may be used, for example up to about 25% by wt. However, without intending to be limited by theory, it is believed that the presence of ionizable groups in the acrylic acid and/or acrylamide co-monomers favors the formation of firm gel structures at even low polymer concentrations. In fact, very firm cryogel structures are formed at about 4% by wt vinyl alcohol co-polymer and 96% by wt water, whereas commonly available vinyl alcohol polymers form firm cryogels at about 14-16% by wt or more PVA.

As the vinyl alcohol co-polymer cryogels according to the invention are formed of emulsifier-free vinyl alcohol co-polymer and may be provided with a firm structure without conventional chemical crosslinking agents, such as glutaraldehyde, toxic components are avoided and the cryogels are advantageous for use in biomedical applications, for example in delivery systems for therapeutic agents and/or cosmetic agents, and as biomedical implants. In the event that firmer hydrogels are desired, traditional crosslinking techniques may used to provide further rigidity to the cryogel through covalent binding after cryogel formation, i.e., by use of conventional chemical crosslinking agents, such as glutaraldehyde, or irradiation.

Alternatively, other methods to modulate the mechanical properties of vinyl alcohol co-polymer cryogels by using non-covalent binders can also be employed. For example, one or more amino acids may be included in the vinyl alcohol co-polymer solution prior to cryogel formation to act as a rheology modifier. Suitable amino acids include, but are not limited to, isoleucine, alanine, leucine, asparagine, lysine, aspartate, methionine, cysteine, phenylalanine, glutamate, threonine, glutamine, tryptophan, glycine, valine, proline, serine, tyrosine, arginine, and histidine. Such amino acids can also serve as a probiotic additive as discussed in further detail below.

Depending on the functional composition of the obtained gel, its properties may greatly vary, e.g. with respect to gel strength and/or rheology. Depending on the functional composition, the produced cryogels may be soft (more suitable for topical preparations or preparations like, but not limited to, wrinkle fillers, and vaginal and rectal injectables) or rigid (more suitable for e.g. oral administration, rectal suppositories or vaginal pessaries), as discussed in further detail below. Further, the functional composition can be varied to control biodegradability of the vinyl alcohol co-polymer cryogel. In one embodiment, the vinyl alcohol co-polymer cryogel is biodegradable, for example over a period of from 1 hour, several hours, one day, several days, one month or several months. In another embodiment, the vinyl alcohol co-polymer cryogel is non-biodegradable. It is well known that PVA is generally biodegradable and does not cause kidney problems when the molecular weight is 18,000 Daltons or below. The molecular weight of the vinyl alcohol co-polymers according to the present invention can be derived from rheology measurements using techniques well known by one of ordinary skill in the art. Due to the presence of ionizable functional groups and random branching of polymer chains, the vinyl alcohol co-polymers and cryogels produced according to the present invention may be biodegradable even when the molecular weight derived from viscosity measurements is well above 18,000 Daltons. Therefore, in vivo tests are necessary to verify the biodegradability of the cryogels for each specific polymer composition. However, it is the general understanding that the present cryogels are prone to biodegradation due to the physical character of bonding between adjacent polymer chains, unlike the covalent bonding produced with chemical cross-linking agents. Therefore, as stated above, in order to obtain non-biodegradable gels, additional use of conventional crosslinking methods may be used after cryotropic treatment, e.g. by creating covalent bonding with chemical crosslinking agents, such as but not limited to, glutaraldehyde, or by radiation.

In one embodiment, the resulting vinyl alcohol co-polymer cryogel may be subjected to freeze-drying according to conventional freeze drying techniques to obtain solid materials with well defined pore structure. The porous materials may be used in various applications including, but not limited to, various solid dosage forms, for example, plugs, for delivery of therapeutic agents or cosmetic agents.

The vinyl alcohol co-polymer cryogels of the invention may optionally be loaded with a therapeutic agent, a cosmetic agent, or a functional agent, as desired. For example, one or more drugs can be loaded into the vinyl alcohol co-polymer cryogels to obtain drug delivery vehicles. The loading of the agents as described may be performed either prior to or post cryogelation. In the former case, the vinyl alcohol co-polymer is dissolved in a solution of the desired agent, for example at a temperature of from about 50° C. to about 80° C., although other temperatures may be employed as appropriate. In a specific embodiment, the vinyl alcohol co-polymer is dissolved in a solution of the desired agent at a temperature of from about 60° C. to about 75° C., or more specifically, from about 62° C. to about 71° C. Alternatively, the agent may be dissolved in the vinyl alcohol co-polymer solution for example at a temperature of from about 50° C. to about 80° C., although other temperatures may be employed as appropriate. In a specific embodiment, the agent is dissolved in a solution of the vinyl alcohol co-polymer at a temperature of from about 60° C. to about 75° C., or more specifically, from about 62° C. to about 71° C. If the cryogel is to be sterilized by autoclavation, the drug dissolution and autoclavation can be combined in one single step. In this case, the dissolution is performed at the autoclavation temperature, typically between 100 and 144° C., depending on the steam pressure used. Following the dissolution of the ingredients, and the autoclavation, if employed, the solution is poured into the desired form and frozen as described above. Upon thawing, a loaded vinyl alcohol co-polymer cryogel formulation is obtained.

Alternatively, the desired agent may be incorporated in the cryogel after the cryogel has been formed, e.g. via soaking of the gel in a solution of the agent. Such incorporation may be conducted prior and/or subsequent to any further crosslinking conducted after cryogel formation, e.g. prior and/or subsequent to any further crosslinking by irradiation, covalent and non-covalent binding.

The loaded agent may comprise a therapeutic agent, a cosmetic agent, and or a functional agent. Examples of therapeutic agents include, but are not limited to, an analgesic, anesthetic, antibacterial, antifungal, anti-inflammatory, anti-itch, anti-allergic, anti-mimetic, immunomodulator, ataractic, sleeping aid, anxiolytic, vasodilator, bone growth enhancer, osteoclast inhibitor, or vitamin. Alternatively, the therapeutic agent may be an amino acid acting as a probiotic additive. In additional embodiments, the therapeutic agent may comprise a biological macrocomplex. Non-limiting examples of biological macrocomplexes include plasmids, viruses, bacteriophage, protein micelles, cell compound organelles such as mytochondriae. In a specific embodiment of the present invention, the vinyl alcohol co-polymer cryogel may be loaded with a sparingly soluble therapeutic agent.

Examples of cosmetic agents include, but are not limited to, coloring components and the like. Examples of functional agents include, but are not limited to, a colorant, taste enhancer, preservative, antioxidant, or lubricant. A thiolated mucoadhesive enhancer may be employed as a functional agent to increase mucoadhesive properties of the cryogel. Thiolated mucoadhesive enhancers are known in the art and include, but are not limited to, cysteine. Additionally, the functional agent may comprise an amino acid rheology modulator as described above. As will be detailed below, such a functional agent may be added to a vinyl alcohol co-polymer solution prior to cryogelation or loaded onto the formed cryogel. Specific embodiments of various loaded vinyl alcohol co-polymer cryogels are described in further detail below.

The vinyl alcohol co-polymer cryogels may be employed in a variety of forms, for example as topical applications, as injectables, embedded as the cryogel or in the form of a dried plug in capsules (hard or soft), formed as thin films, for example for topical application, mucoadhseive films, for example for buccal or sublingual drug delivery, a suppository, e.g. for rectal or vaginal delivery, as a base for chewing gum, for example for drug or cosmetic agent delivery, biomedical implants (with or without loaded agent), and the like. Specific, non-limiting examples are described below.

In one embodiment, the cryogel is freeze dried and loaded with a therapeutic agent to form a solid plug. Such a plug may be used in various applications. In one embodiment, the plug may be used as a floating drug delivery vehicle in the stomach. The drugs incorporated in this device may include, but are not limited to, caffeine, theophylline, dilthiazem, propranolol hydrochloride, bipyridine, tramadol, and omeprazol. In another embodiment, the plug may be employed as a carrier for a nicotine inhalator, for example to provide smoke-free nicotine administration, for example to aid in smoking cessation. In a specific embodiment, the freeze-dried solid porous plugs of vinyl alcohol co-polymer cryogel are loaded with nicotine from a nicotine ethanol solution by using a rotary-evaporation. The nicotine-loaded solid plug is then integrated in an inhalator device, for example a short pipe with a mouthpiece to allow imitation of the puffing action of smoking.

Another embodiment of the present invention includes a drug-containing topical formulation. For example, in a more specific embodiment, the topical formulation may be used, e.g., prior to or for wound treatments, for burn healing, for treatment of insect bites, for soreness in connection with breast feeding, or for rectal problems such as hemorrhoids and cracks. The combination of high water content and slow drug release in a loaded vinyl alcohol co-polymer cryogel according to the invention is highly advantageous for such topical preparations. The cryogel may be formed as a soft hydrogel which releases the incorporated drug slowly and that has a very high water content. In a specific embodiment, the cryogel formulation is loaded with an antibiotic, antiseptic or antifungal drug and dried into a thin film which swells when in contact with exudates and therefore, not only covers the wound, but also exhibits good adhesion to its surface. The swelling of the film commences the sustained release of the loaded drug. Suitable drugs include, but are not limited to, nitrofurazone, fusidic acid, mafenide, iodine, bacitracin, lidocain, bupivacain, levobupivakain, prilocain, ropivacain, mepivacain, and aloe vera.

In another specific embodiment, the cryogel formulation is used in topical formulations for local pain relief, anti-inflammatory treatment or deep heating liniments. The drug may include, but is not limited to, diclofenac sodium, salicylic acid and methyl salicylate.

In another embodiment, the vinyl alcohol co-polymer cryogel may be used for treatment of psoriasis, eczema, and other forms of dermatitis treatment. The drug may include, but is not limited to, an interleukin-6 antagonist, an anti-inflammatory drug, corticosteroids, immunomodulators like pimecrolimus and tacrolimus, anti-itch drugs like capsaicin and menthol, and naloxone hydrochloride and dibucaine.

An additional embodiment of the invention is directed to a mucoadhesive formulation. The mucoadhesive formulation may be use, for example, for buccal, palatal or sublingual drug delivery. The vinyl alcohol co-polymer cryogel is loaded with a drug and dried to a thin film form and rapidly swells when in contact with water, thereby exhibiting excellent mucoadhesive properties. The mucoadhesion increases the retention time of the formulation in the oral cavity and ensures intimate contact with the underlying mucus and rapid onset of action. In a specific embodiment, the mucoadhesive formulation is formed from a cryogel prepared from the vinyl alcohol co-polymer as described, optionally including a thiolated mucoadhesive enhancer, for example, but not limited to, cysteine, which serves to enhance mucoadhesion. In another specific embodiment, the mucoadhesive formulation contains, inter alia, ataractic, sleeping aid or anxiolytic drugs, examples of which include, but are not limited to, diazepam, oxazepam, lorazepam, alprazolam, buspirone, flurazepam, propiomazine, triazolam, nitrazepam, eszopiclione, zoplclone, modafinil, ramelteon, zaleplon, melatonin, valerian root, st john's wort, restoril, sodium oxybate, midazolam, zolpidem, and diphenhydramine hydrochloride.

Another embodiment of the present invention is directed to a mucoadhesive film for palatal use for mild local anesthesia in dentistry. In a specific embodiment, the mucoadhesive film is formed from a cryogel prepared from the vinyl alcohol co-polymer as described, optionally including a thiolated mucoadhesive enhancer, for example, but not limited to, cysteine, which, as noted previously, serves to enhance mucoadhesion. Suitable drugs may include, but are not limited to, anesthetics such as lidocain, bupivacain, levobupivakain, prilocain, ropivacain, and mepivacain. A further specific embodiment of mucoadhesive formulations contain a histamine antagonist useful, e.g., for rapid treatment of allergic reactions, motion sickness, nausea in pregnancy and cancer. Anti-allergic substances include, but are not limited to, clemastine, fexofenadine, loratidine, acrivastine, desloratidine, cetrizine, levocetrizine, mizolastine. Antimemetic drugs useful for treatment of motion sickness and nausea may include, but are not limited to, promethazine, cinnarizine, cyclizine, and meclizine. Another specific embodiment includes a mucoadhesive formulation for cardiac treatment. The drug may include, but is not limited to, a vasodilator such as isosorbide dinitrate or nitroglycerine.

Another embodiment of the present invention includes pH sensitive cryogel systems, for example, for providing controlled drug release. The sensitivity of the cryogel may be tuned by the optimal balance of introduced ionizable functional groups which not only influence the strength of the produced gel but also the swelling behavior and thus the release of incorporated drugs in various pH. In a specific embodiment, the pH sensitive cryogel system is a solid plug or cryogel that optionally is embedded in a soft or hard capsule. In a more specific embodiment, the pH sensitive cryogel system is a vaginal hydrogel formulation.

Another embodiment of the present invention includes a drug-containing thermosensitive cryogel. The sensitivity of the cryogel to changes in temperature is achieved by introducing lipophillic side chains (e.g. methyl-, ethyl-, propyl-acrylate/acrylamide derivatives). In a more specific embodiment, the thermosensitive cryogel liquefies at body temperature.

A further embodiment of the present invention includes a rectal cryogel formulation. The drugs may include, but are not limited to, indomethacin, paracetamol, diazepam, propranolol, and atenolol. The formulation has the advantage of having a high water content and suitable consistency. Yet another embodiment of the present invention includes an injectable soft cryogel formulation for rectal use for treatment of ulcerative colitis. The drugs include, but are not limited to, 5-aminosalicylic acid (mesalazine) or its derivatives.

Another embodiment of the invention is in the form of a vaginal hydrogel formulation. The drug may include, but is not limited to, an antifungal or antibiotic such as ekonazole, metronidazol, and/or clotrimazol (klotrimazol). The formulation has the advantage of having a high water content and suitable consistency.

Another embodiment includes a formulation based on the cryogel material produced according to the present invention and useful as a vaginal solid plug. The drug may include, but is not limited to, ekonazole, metronidazol, and klotrimazol.

An additional embodiment of the present invention includes a formulation containing one or more analgesics loaded in the cryogel for pain relief. Suitable analgesic drugs include, but are not limited to, morphine, codeine, oxycodone, fentanyl, thebaine, methadone, ketobemidone, pethidine, tramadol, propoxyphene, hydromorphone, hydrocodone, oxymorphone, desomorphine, diacetylmorphine, nicomorphine, dipropanoylmorphine, benzylmorphine and ethyl morphine.

In a further embodiment of the present invention, the vinyl alcohol co-polymer cryogel is formed as a biomedical implant, for example, an orthopedic implant. Non-limiting examples of orthopedic implants include, but are not limited to, artificial disks, meniscus implants, and cochlear implants. The cryogel system is molded to the preferred shape and may optionally be loaded with a therapeutic agent. The polymer solution is sterilized prior to or post cryogelation, preferably prior to and by autoclavation. Non-limiting examples of drugs suitable for use include, but are not limited to, bone morphogenetic proteins, antibiotics such as gentamicin, tobramycin, amoxicillin and cephalothin, and bisphosphonates such as pamidronate, neridronate, olpadronate, alendronate, ibandronate, risedronate, and zoledronate. In a specific embodiment, the vinyl alcohol co-polymer solution from which the biomedical implant cryogel is formed contains one or more amino acids serving as both a rheology modulator and a probiotic additive. One or more of the amino acids noted above may be employed.

In additional embodiments of the present invention, the vinyl alcohol co-polymer cryogel may be employed as a biodegradable implant, for example, for bone regeneration. The cryogel may be molded to a desired shape as a macroporous tissue scaffold and may optionally be loaded with, for example, bone growth enhancers, drugs that inhibit osteoclast action and the resorption of bone, drugs that stimulate bone in growth, growth factors, and cytokines having the ability to induce the formation of bone and cartilage, as well as antibiotics. The co-polymer solution is sterilized prior to or post cryogelation, preferably prior to cryogelation and by autoclavation. Non-limiting examples of suitable drugs suitable for loading include, but are not limited to, bone morphogenetic proteins, antibiotics such as gentamicin, tobramycin, amoxicillin and cephalothin, and bisphosphonates such as pamidronate, neridronate, olpadronate, alendronate, ibandronate, risedronate, and zoledronate. In a specific embodiment, the vinyl alcohol co-polymer solution from which the biodegradable implant cryogel is formed contains one or more amino acids serving as both a rheology modulator and a probiotic additive. One or more of the amino acids noted above may be employed.

Another embodiment of the present invention is directed to biomedical implants comprising sterile implantable macroporous cryogels for delivery of biological macrocomplexes. Non-limiting examples of biological macrocomplexes include plasmids, viruses, bacteriophage, protein micelles, and cell compound organelles such as mytochondriae. The polymer solution is sterilized prior to or post cryogelation, preferably prior to cryogelation and by autoclavation. In a specific embodiment, the vinyl alcohol co-polymer solution from which the biodegradable implant cryogel is formed contains one or more amino acids serving as both a rheology modulator and a probiotic activity. Suitable amino acids include those described in detail above.

A further embodiment of the present invention includes various sterile cosmetic biodegradable fillers and/or implants. These systems for cosmetic use may be either firm (implantable) or soft (injectable). They may further be loaded with vitamins, e.g. C, E, or A, or other probiotic substances. Non-limiting examples of biodegradable fillers and implants are wrinkle fillers, breast augmentation implants, butt implants, facial implants such as cheek implants, and the like.

The following Examples demonstrate non-limiting embodiments of various aspects of the invention.

Example 1

In this example, a vinyl acetate co-polymer was prepared from the following dispersion:

| | |
|---|---|
| Vinyl acetate | 86 ml |
| Acrylamide | 7.1 g |
| Methacrylic acid | 8.6 g |

-continued

| | |
|---|---|
| NaHCO₃ | 1 g |
| Ammonium persulfate | 0.3 g |
| Water | 150 ml |

A three-neck reaction vessel, connected to a chiller and a mixer, was placed in a water bath. The vessel was filled with 86 g of vinyl acetate, 7.1 g acrylamide, 7.1 g of methacrylic acid, 1.0 g sodium hydrocarbonate, 140 ml water, and 0.3 g ammonium persulfate, previously dissolved in 10 ml of water. The reagents were allowed to stand under slow stirring for 5-6 hours at 64-70° C. until a white emulsion was formed and the residual monomer concentration did not exceed 0.4% by wt. The produced emulsion contained 40.1% by wt solids and exhibited pH of 4.4 and viscosity of 16.5 Pa·s. The resulting copolymer viscous white emulsion was then chilled and further saponified in alkali medium using the following mixture wherein the dispersion refers to the copolymer emulsion product:

| | |
|---|---|
| Dispersion | 180 ml |
| Water | 240 ml |
| Ethanol | 1800 ml |
| NaOH | 24 g |

Specifically, 180 ml of the emulsion was diluted with 240 ml of water and loaded in the vessel containing 24 g of sodium hydroxide in 1800 ml of ethanol. At 20° C., a powder PVA was precipitated and acetic acid was added to the mixture under stirring to neutralize the alkali. The vinyl alcohol co-polymer was then filtered and the crude product was thoroughly washed with ethanol and subsequently dried. 50.62 g of product was yielded. The viscosity of 1% by wt solution of the obtained product at 20° C. was 12.5 mPa·s, intrinsic viscosity $[\eta]=1.5$. The resultant vinyl alcohol co-polymer product contained 2.3% by wt acetate groups, 9.24% by wt carboxylate groups, 1.35% by wt carboxylic groups, and 4.75% by wt amide groups.

Example 2

In this example, a vinyl acetate co-polymer was prepared from the following dispersion:

| | |
|---|---|
| Vinyl acetate | 86 ml |
| Acrylamide | 7.1 g |
| Acrylic acid | 7.2 g |
| NaHCO₃ | 0.75 g |
| benzoyl peroxide | 0.12 g |
| ammonium persulfate | 0.23 g |
| Water | 152 ml |

A three-neck reaction vessel as described was placed in a water bath and loaded with 86 ml of vinyl acetate, 7.1 g acrylamide, 7.2 g of acrylic acid, 0.75 g sodium hydrocarbonate, 190 ml water, 0.12 g of benzoyl peroxide, and 0.23 g ammonium persulfate, previously dissolved in 10 ml of water. The reagents were allowed to stand under slow stirring for 4 hours at 64-70° C. until a white emulsion was formed and the residual monomer concentration did not exceed 0.4% by wt. The produced emulsion contained 39.5% by wt solids and exhibited pH=3.8 and viscosity of 38.5 Pa·s. The viscous white emulsion was then chilled and further saponified in alkali medium using the following mixture wherein the dispersion refers to the copolymer emulsion product:

| | |
|---|---|
| Dispersion | 180 ml |
| Water | 240 ml |
| Ethanol | 1500 ml |
| NaOH | 24 g |

180 ml of the emulsion was diluted with 240 ml of water and loaded in the vessel containing 24 g of sodium hydroxide in 1500 ml of ethanol. The emulsion was loaded into the reactor drop-wise and stirred. At 20° C., a powder vinyl alcohol co-polymer was precipitated and acetic acid was added to the mixture under stirring to neutralize the alkali. The vinyl alcohol co-polymer was then filtered and the crude product was thoroughly washed with ethanol and subsequently dried. 50 g of product was yielded. The viscosity of 1% by wt solution of the obtained product at 20° C. was 50 mPa·s, intrinsic viscosity $[\eta]=3.05$. The resultant vinyl alcohol co-polymer product contained 3.97% by wt acetate groups, 8.55% by wt carboxylate groups, and 5.57% by wt amide groups.

Example 3

In this example, a vinyl acetate co-polymer was prepared from the following dispersion:

| | |
|---|---|
| Vinyl acetate | 160 ml |
| Acrylamide | 25 g |
| NaHCO3 | 1.3 g |
| Potassium persulfate | 0.5 g |
| Water | 350 ml |

A three-neck reaction vessel as described was placed in a water bath and was filled with 160 ml of vinyl acetate, 25 g acrylamide, 1.3 g sodium hydrocarbonate, 330 ml water, and 0.5 g potassium persulfate, previously dissolved in 20 ml of water. The reagents were allowed to stand under slow stirring for 3.5 hours at 64-70° C. until a white emulsion was formed and the residual monomer concentration did not exceed 0.4% by wt. The produced emulsion contained 32.5% by wt solids and exhibited pH=5.1 and viscosity of 45.24 Pa·s. The viscous white emulsion was then chilled and further saponified in alkali medium using the following mixture wherein the dispersion refers to the copolymer emulsion product:

| | |
|---|---|
| Dispersion | 180 ml |
| Water | 240 ml |
| Ethanol | 1800 ml |
| NaOH | 24 g |

180 ml of the emulsion was diluted with 240 ml of water and loaded in the vessel containing 24 g of sodium hydroxide in 1800 ml of ethanol. The emulsion was loaded into the reactor drop-wise and stirred. At 20° C., a powder vinyl alcohol co-polymer was precipitated and acetic acid was added to the mixture under stirring to neutralize the alkali. The vinyl alcohol co-polymer was then filtered and the crude product was then thoroughly washed with ethanol and subsequently dried. 37.46 g of product was yielded. The viscosity of 1% by wt solution of the obtained product at 20° C. was 10.7 mPa·s, intrinsic viscosity $[\eta]=1.61$. The resultant vinyl alcohol co-polymer product contained 6.02% by wt acetate groups, 1.97% by wt carboxylate group, and 13.63% by wt amide groups.

Characterization of Materials from Examples 1, 2, and 3

The three vinyl alcohol co-polymer compositions described in Examples 1-3 herein, denoted as PVA-1, PVA-2, and PVA-3, respectively, were characterized to show the dependence of the cryogel properties on the functional composition. PVA-1 was a copolymer of vinyl alcohol with acrylamide and methacrylic acid, PVA-2 was a copolymer of vinyl alcohol with acrylamide and acrylic acid, and PVA-3 was a copolymer of vinyl alcohol with acrylamide. The characteristic (intrinsic) viscosities of the samples in 0.05M $NaNO_3$ were 1.61, 3.05, and 1.5 dl/g for PVA-1, PVA-2, and PVA-3, respectively, and the average degree of saponification was 94-97%. To form cryogels, 0.4 g of each vinyl alcohol co-polymer was dissolved in 10 ml of deionized water at 80° C. under stirring. The clear solution was then frozen at −22° C. overnight and thawed at room temperature. The produced gels were subsequently used for analysis.

Figure 1B:
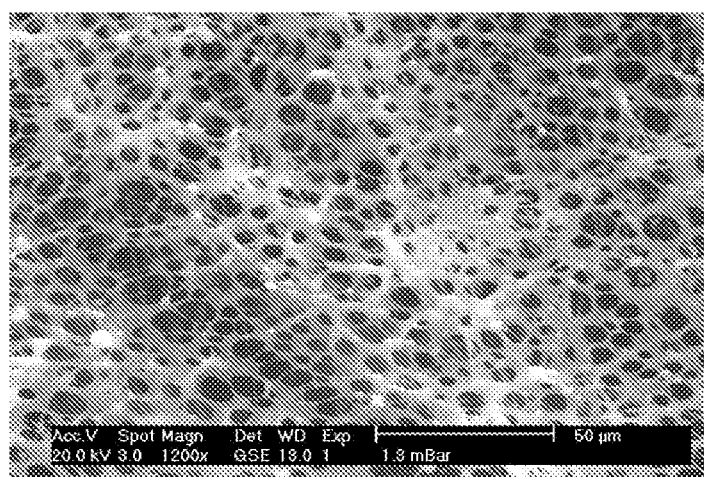
Figure 1C:
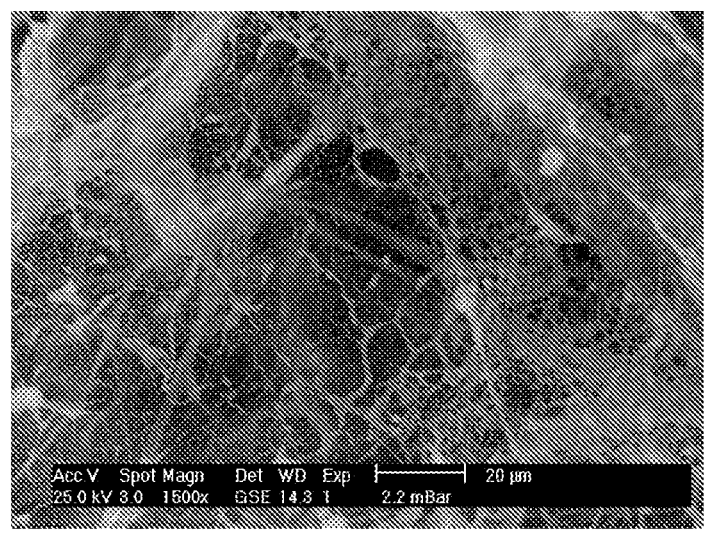

The vinyl alcohol co-polymer cryogels were visualized using environmental scanning electron microscopy (ESEM) (Philips XL30 SEM) equipped with a Peltier cooling stage. No fixating agents such as glutaraldehyde or osmium tetraoxide were used. The cryogels were soaked in water and placed in the ESEM chamber. The temperature of the Peltier stage was fixed at −7° C. to freeze the sample. When frozen, the pressure in the chamber was set to 5 mBar and acceleration voltage was applied (20 or 25 kV). The pressure in the chamber was dropped then to 1 mBar to induce sublimation of frozen water. ESEM is an electron microscopy technique which allows the examination of hydrated samples. However, when pores in a hydrogel are filled with water, which constitutes up to 96% of mass, their structure is difficult to visualize. Further, due to capillary forces, the structure collapses into a dense compact upon removal of water. The use of fixating agents such as glutaraldehyde and osmium tetraoxide, which are commonly used in electron microscopy, is not preferable because glutaraldehyde is a known cross-linking agent for PVA. To avoid the collapse of structure upon drying, the gel samples were first frozen, and then water was sublimed leaving the pore structure intact. In FIGS. 1A-1C, the gel macropore structure can be visualized. As it is seen in these pictures, the pores in PVA-1 sample were in the order of 10-15 µm, and an open sponge-like structure was clearly visible. The pores in PVA-2 sample were considerably smaller than in PVA-1 (about 7 µm). Further, the pore walls were thicker than in PVA-1 and their distribution appeared denser. The smallest pores were observed in PVA-3, which were in the range of 2 µm only. The pore walls were generally thin though occasionally thick structures were visible.

Figure 2:
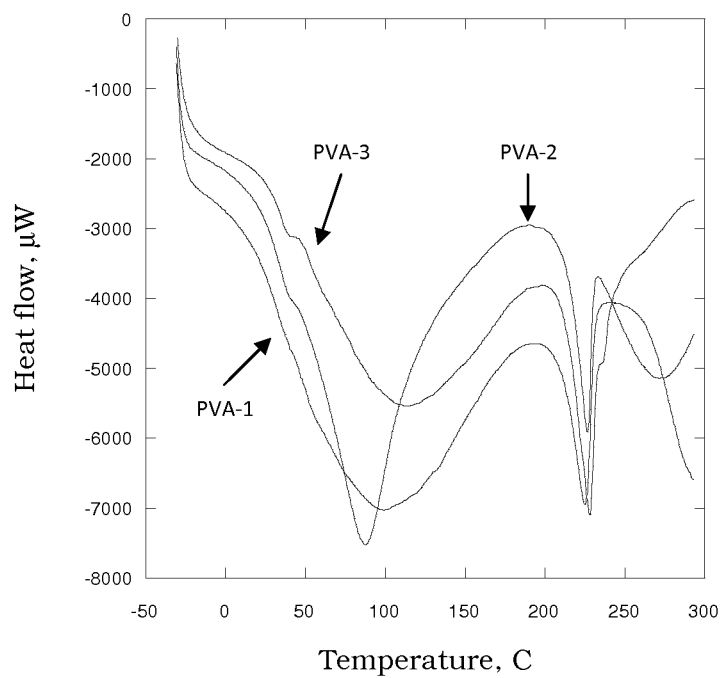
FIG. 2 shows differential scanning calorimetry (DSC) results of cryogels of Examples 1-3.
Figure 3A:
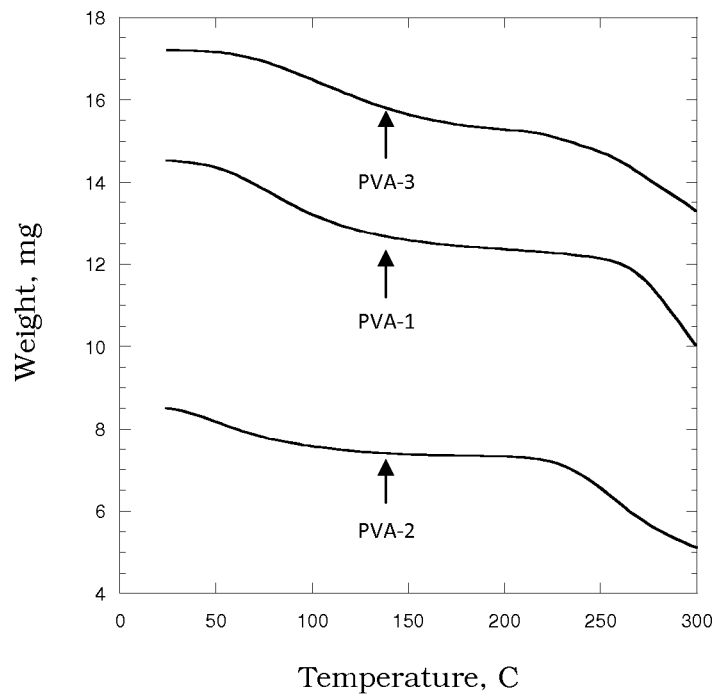
FIGS. 3A and 3B show thermogravimetric analysis (TGA) results of cryogels of Examples 1-3.
Figure 3B:
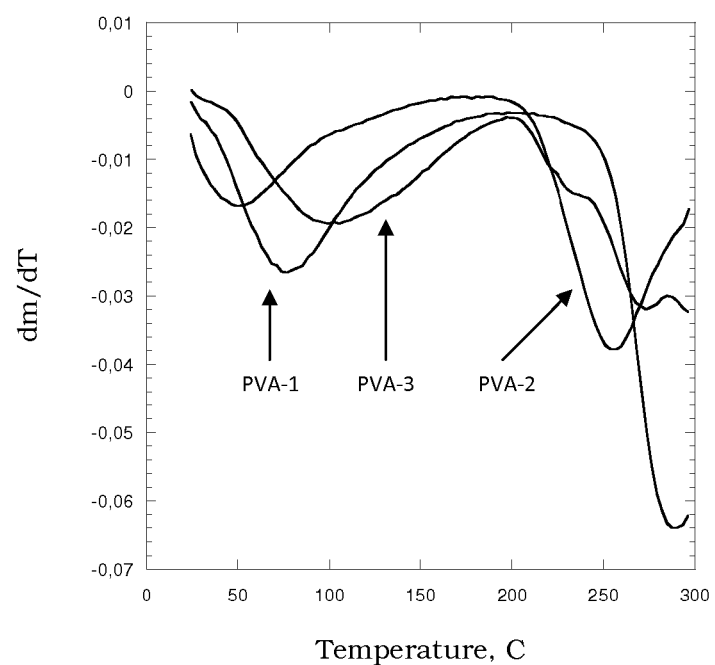

The thermal properties of the co-polymers were studied. A Seiko DSC 220 (SSC/5200 h, Seiko, Japan) was used for differential scanning calorimetry (DSC). The instrument was calibrated for melting point Tm(° C.) and heat of fusion ΔHm (J/g) of indium (156.60° C.; 28.59 J/g), tin (232° C.; 60.62 J/g), gallium (29.80° C., 80.17 J/g), and zinc (419° C., 111.40 J/g). The experiments were performed in $N_2$ atmosphere. The heating rate was 10° C./min. The original co-polymer samples were carefully weighed in aluminum pans with cover (TA Instruments, Delaware, USA). Empty pans were used as reference. A TGA/SDTA 581e (Mettler Toledo, Switzerland) instrument was used for thermogravimetric analysis (TGA). The experiments were performed in air atmosphere. The heating rate was 10° C./min. The original polymer samples were carefully weighed in open 70 µl aluminum oxide crucibles. The amount of moisture was calculated as weight loss at 100° C. In FIG. 2, the DSC plot is presented (the lower plot is the first derivative). Because cryogels consisted of 96% by wt water, the DSC and TGA profiles would be totally dominated by evaporation of water. Therefore, DSC and TGA analysis were performed on the original co-polymers without cryotropic gelation. Prior to DSC analysis, the samples were cooled to −30° C. As the temperature is raised, the water present in the sample first melts and then starts to evaporate. At around 100° C., there is a large endothermic peak seen in all samples corresponding to water evaporation. Upon further heating, at around 230° C., there is the second large endothermic peak seen, which corresponds to a melting point of PVA. Further heating induces pyrolysis. It should be noted that at least in two samples (PVA-2 and PVA-3) there is a small phase transition peak detected at around 40° C. The glass transition temperature of pure PVA is 81° C., and the depression of Tg in these samples could be a complex response to plasticizing action of moisture and presence of functional groups. In FIGS. 3A and 3B, the TGA results are presented (the lower plot is the first derivative). The TGA revealed that the moisture content of PVA-1, PVA-2, and PVA-3 was 7.25, 11.05, and 4.13% by wt, respectively.

Figure 4A:
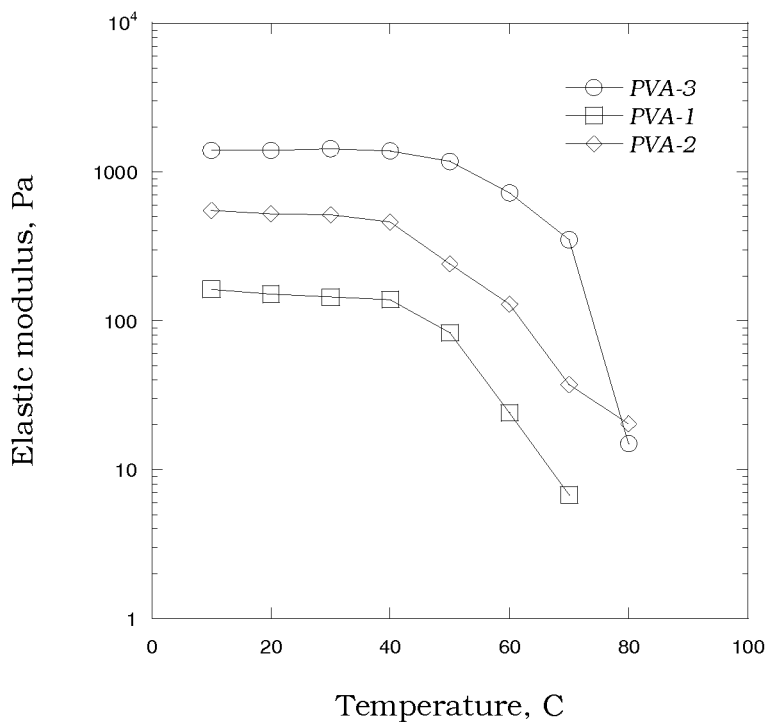
FIGS. 4A and 4B show dynamic mechanical thermal analysis (DMTA) results of cryogels of Examples 1-3.
Figure 4B:
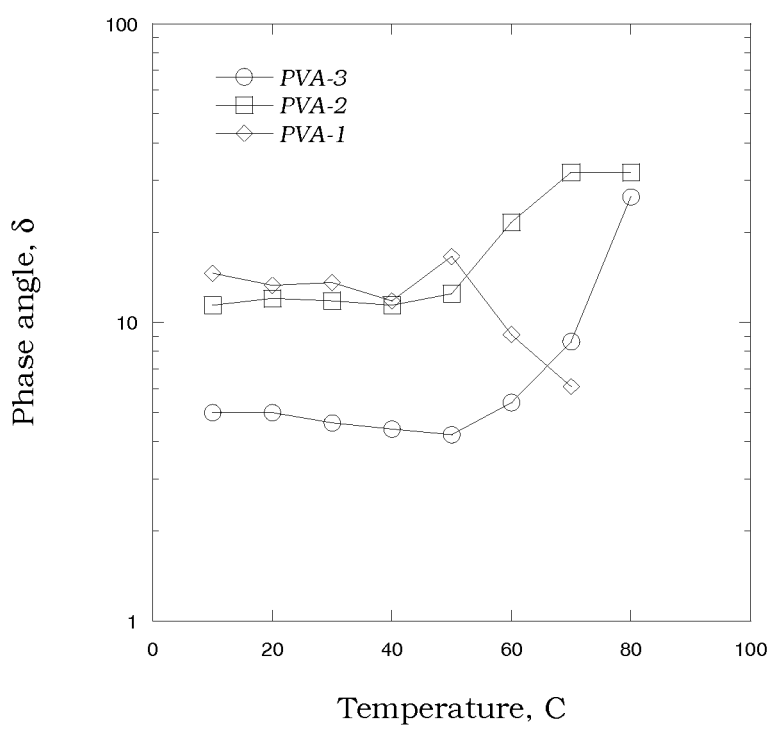

Dynamic mechanical thermal analysis (DMTA) was performed to characterize the rheological properties of the cryogels. This was done using a controlled rate instrument of the couette type in the dynamic oscillation mode (Bohlin VOR Reometer, Bohlin Reologi, Sweden) at 1 Hz. The measuring system was a concentric cylinder, C14 type. A 4.13 mm torsion wire was used for analysis. Silicone oil was used on the top of the sample to prevent evaporation. It was ascertained that the applied strain was in the linear viscoelastic region. The measurements were conducted at 20, 30, 40, 50, 60, and 70° C., respectively. The phase angle δ is defined as follows:

$$\tan\delta = G''/G' \quad (1)$$

where G' is the elastic (storage) modulus and G" is the viscous (loss) modulus. In FIGS. 4A and 4B, the rheological properties of the vinyl alcohol co-polymer cryogels are presented. In FIG. 4A, the elastic modulus of the cryogels is plotted as a function of temperature. In the PVA-1 and PVA-2 samples, the elastic modulus G' is constant in the range between 10 and 40° C., whereas at higher temperatures the value of G' is falling. In the PVA-3 sample, the drop in the value of the elastic modulus G' occurs at around 50° C. The higher the value of G', the more resilient is the gel. It is seen from this plot that PVA-1 formed the weakest gel in the series. The strongest gels were formed by PVA-3 followed by PVA-2. In FIG. 4B, the phase angle δ is plotted as a function of temperature. Traditionally, the temperature at which the phase angle δ exhibits a maximum is defined as the glass transition temperature of a polymer. It should be noted that, at temperatures above 80° C., the polymers are completely dissolved. It can thus be concluded from this plot, that PVA-1 exhibits a Tg at around 50° C., whereas the Tg values for PVA-2 and PVA-3 are about 70° C. and 80° C., respectively. However, the onset of the phase transition in PVA-2 and PVA-3 samples is observed at around 50° C., which is in accordance with the DSC results in FIG. 2. The values of phase angle below 10° are typical for strong gel structures. In the range between 10 and 40° C., it is seen that PVA-1 forms very weak gel structures as indicated by both high values of phase angle δ and low values of elastic modulus G'. The low values of phase angle δ for PVA-3 in the range between 10 and 50° C. are indicative of a strong gel, whereas the gel properties of PVA-2 are intermediate between PVA-1 and PVA-3. It should be noted that stronger gel structure was associated with smaller pore size and higher density of pores visualized in ESEM.

Figure 5A:
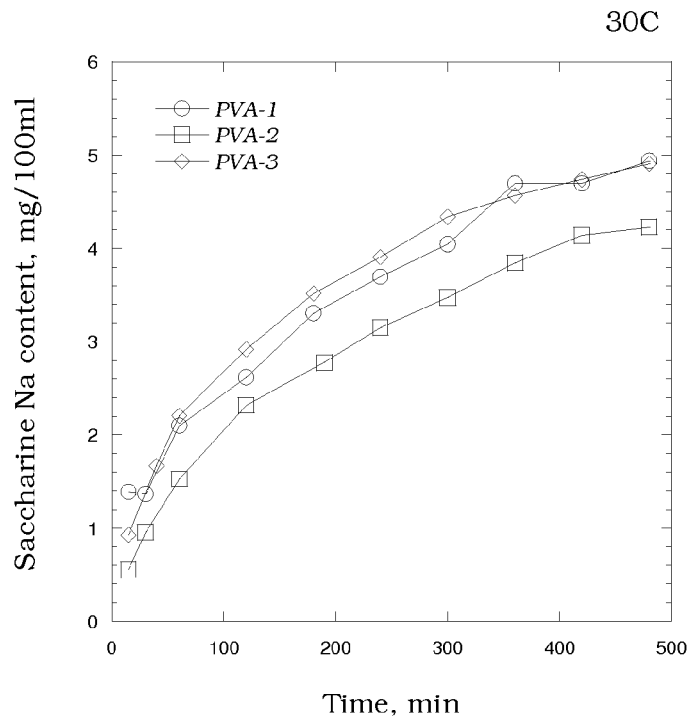
FIGS. 5A and 5B show saccharine sodium release from cryogels of Examples 1-3 studied by UV-spectroscopy.
Figure 5B:
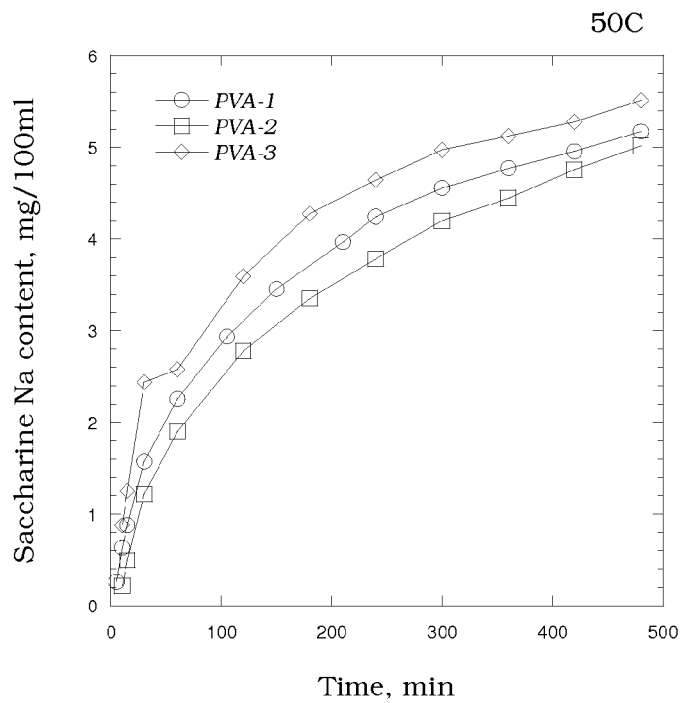

In order to investigate the drug release properties from cryogels, saccharine sodium, as a model substance, was loaded in the cryogels. 50 mg of saccharine sodium was dissolved in deionized water and the total volume was brought to 50 ml. 5 ml of stock solution was placed in a 10 ml glass vial and 0.2 g of the vinyl alcohol co-polymer was added. The solution was heated to 80° C. until the co-polymer was dissolved and frozen at −22° C. overnight. The samples were thawed at room temperature. The produced cryogel samples were cylindrical in shape (2 cm in height; 2.3 cm in diameter). A glass beaker was filled with 100 ml of deionized water and heated to 30 or 50° C., respectively. The cryogel samples were placed in the beaker and the saccharine sodium release was monitored with UV-spectrophotometer (UV 1650PC, Shimadzu, Japan) at 270 nm. In FIGS. 5A and 5B, the release profiles of saccharine sodium from the vinyl alcohol co-polymer cryogels are presented. Saccharine sodium was released most rapidly from PVA-3 sample followed by PVA-1. The slowest release profiles were observed in PVA-2. No direct correlation between the gel strength or pore size is made. It has previously been observed that depending on the chemical nature of the drug substance, various interactions between the PVA and drug can be observed. Because saccharine sodium is an ionized molecule, the differences in the release profiles could be due to various electrostatic interactions with the PVA-composites.

Figure 6:
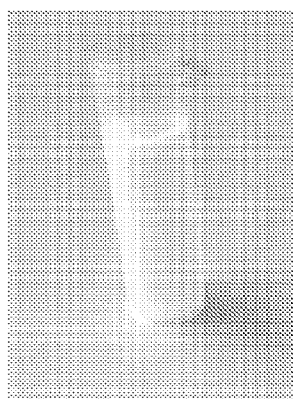
FIG. 6 shows homogeneous distribution of a dye (fluorescin sodium) within the matrix of a cryogel.

To verify that incorporated drugs are being homogeneously distributed in the cryogel formulation, fluorescin sodium was incorporated in PVA-3 in the same way as described above for saccharine sodium incorporation. 5 wt % cryogel was used. FIG. 6 shows that the yellow dye was homogeneously dispersed in the cryogel matrix.

Example 4

In this example, a vinyl acetate co-polymer was prepared from the following dispersion:

| | |
|---|---|
| Vinyl acetate | 86 ml |
| Acrylic acid | 14.5 g |
| NaHCO3 | 0.8 g |
| Potassium persulfate | 0.1 g |
| Water | 150 g |

A three-neck reaction vessel as described was placed in a water bath and was filled with 86 g of vinyl acetate, 14.5 g of acrylic acid, 0.8 g sodium hydrocarbonate, 140 ml water, and 0.1 g potassium persulfate, previously dissolved in 10 ml of water. The reagents were allowed to stand under slow stirring for 4.5 hours at 64-70° C. until a white emulsion was formed and the residual monomer concentration did not exceed 0.4% by wt. The produced emulsion contained 40.1% by wt solids and exhibited pH=3.2 and viscosity of 9.78 Pa·s. The viscous white emulsion was then chilled and further saponified in alkali medium using the following mixture wherein the dispersion refers to the copolymer emulsion product:

| | |
|---|---|
| Dispersion | 30 ml |
| Water | 30-40 ml |
| Ethanol | 300 ml |
| NaOH | 4 g |

30 ml of the emulsion was diluted with 40 ml of water and loaded in the vessel containing 4 g of sodium hydroxide in 300 ml of ethanol. The emulsion was loaded into the reactor drop-wise and stirred. At 20° C., a powder vinyl alcohol co-polymer was precipitated and acetic acid was added to the mixture under stirring to neutralize the alkali. The vinyl alcohol co-polymer was then filtered and the crude product was thoroughly washed with ethanol in and subsequently dried. 6.1 g of product was yielded. The viscosity of 1% by wt solution of the obtained product at 20° C. was 46.02 mPa·s, intrinsic viscosity [η]=1.5. The resultant PVA product contained 6.49% by wt acetate groups, 21.17% by wt carboxylate groups.

Example 5

Figure 7A:
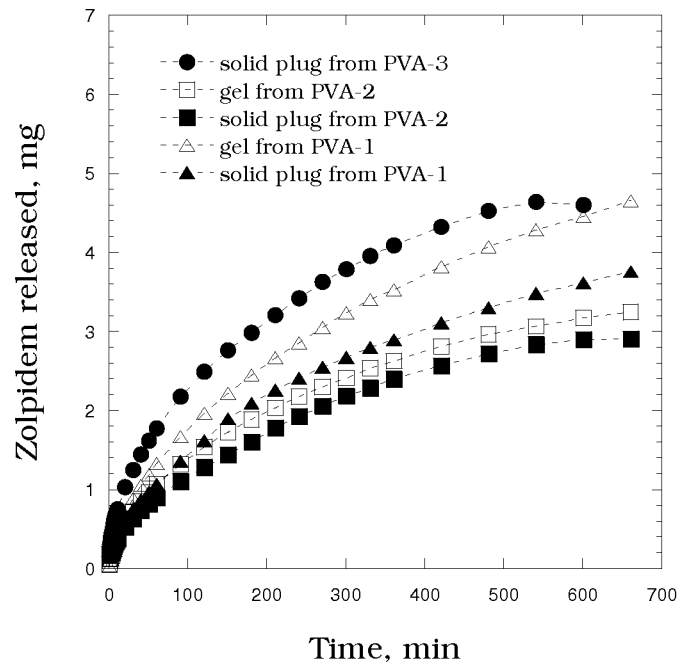
FIGS. 7A and 7B show Zolpidem release from cryogels of Examples 1-3 studied by UV-spectroscopy, with FIG. 7A showing sustained release of Zolpidem in 0.9% sodium chloride solution and FIG. 7B showing the effect of pH on Zolpidem release.
Figure 7B:
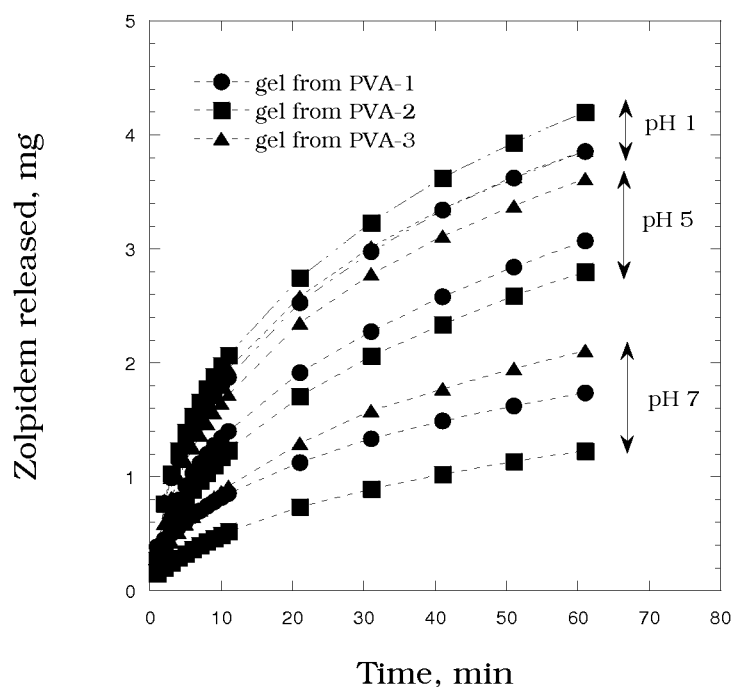

The vinyl alcohol co-polymers in Examples 1, 2 and 3 (i.e. PVA-1, PVA-2 and PVA-3) were dissolved in water at 64° C. to produce 5% vinyl alcohol co-polymer solutions. Zolpidem drug was added in the above solution. 3 ml of the obtained solution containing 5 mg of Zolpidem was poured into a cylindrical form and frozen overnight at −30° C. The forms were thawed at room temperature to obtain ready to use cryogels for oral use. Similarly, solid plugs were produced by freeze drying over night. The release profiles of Zolpidem from the different formulations and at different pHs are shown in FIGS. 7A and 7B.

Example 6

Figure 8A:
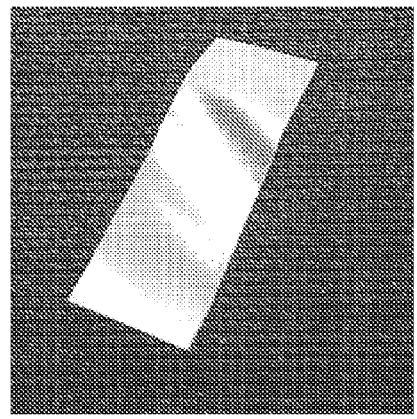
FIGS. 8A and 8B show, respectively, a mucoadhesive film for buccal drug delivery prior to application and applied to a lower lip.
Figure 8B:
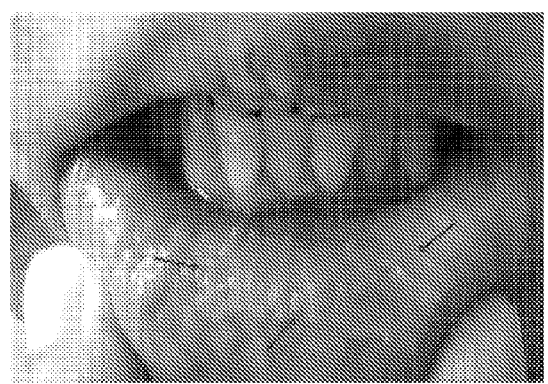

The material in Example 3 (PVA-3) was dissolved in water at 64° C. to produce 5% modified vinyl alcohol co-polymer solution. Diazepam drug was added in the above solution. 3 ml of the obtained solution containing 5 mg of diazepam was poured in a shallow form and frozen overnight at −30° C. The form was thawed at room temperature and dried to a constant mass to produce a thin film (0.2-0.5 mm) The film is ready for use as a mucoadhesive drug delivery vehicle for buccal use. FIGS. 8A and 8B show the physical appearance of the film prior to use as well as at the site of application in vivo.

Example 7

The material in Example 2 (PVA-2) is loaded with theophylline, freeze-dried and formulated in hard capsules. 5% by wt cryogel is used, and the drug is incorporated as described in Example 5. The formulation is intended for a floating drug delivery vehicle in the stomach.

Example 8

The material in Example 1 (PVA-1) is loaded with lidocain and is for use in a topical preparation for burn healing. The inventive vinyl alcohol co-polymer is used to form a soft hydrogel which releases the incorporated drug slowly and which has significantly higher water content than its analogues. 3.5% by wt cryogel is used. The drug is incorporated as in Example 5.

Example 9

The material from Example 2 (PVA-2) is loaded with nitrofurazone for wound healing. 5% by wt cryogel containing the drug is prepared and molded in thin films (0.2-0.5 mm), which are then dried to a constant mass. The film is intended for use as a mucoadhesive drug delivery vehicle which swells when in contact with exudates from the wound, which in turn commences the release of nitrofurazone.

Example 10

The material in Example 1 (PVA-1) is loaded with diclofenac sodium and is intended for use as a topical preparation for local pain relief. 4% by wt cryogel is used. The drug is incorporated as in Example 5.

Example 11

The material in Example 1 (PVA-1) is loaded with an interleukin-6 (IL-6) antagonist (sample 11a) and cortisone (sample 11b), for psoriasis treatment. 3.8% by wt cryogel is used. The drug is incorporated as in Example 5.

Example 12

The material in Example 3 (PVA-3) is loaded with indomethacin to form a rectal firm hydrogel formulation. The formulation has the advantage of having high water content and suitable elasticity. 7% by wt cryogel is used. The drug is incorporated as in Example 5.

Example 13

The material in Example 3 (PVA-3) is loaded with methronidazole to form a firm hydrogel formulation for vaginal application. The formulation has the advantage of having high water content and suitable firmness and elasticity. 7% by wt cryogel is used. The drug is incorporated as in Example 5.

Example 14

In this example, a vinyl acetate co-polymer was prepared from the following dispersion using the procedure of Example 1:

| | |
|---|---|
| Vinyl acetate | 160 ml |
| Ethacrylamide | 25 g |
| NaHCO$_3$ | 1.3 g |
| Potassium persulfate | 0.5 g |
| Water | 350 ml |

The product was saponified in alkali medium using the following mixture wherein the dispersion refers to the copolymer emulsion product, using the procedure of Example 1:

| | |
|---|---|
| Dispersion | 180 ml |
| Water | 240 ml |
| Ethanol | 1800 ml |
| NaOH | 24 g |

7% by wt polymer hydrogel is used as a thermoresponsive gel-forming matrix for rectal drug administration of indomethacin.

Example 15

The material in Example 4 is used to produce biodegradable injectable fillers (for example, wrinkle fillers, etc.) having a soft consistency. 4% by wt polymer cryogel is used. Prior to cryogelation, the polymer is autoclaved and sterilized. In one trial, the filler is loaded with vitamin C.

Example 16

A biodegradable implantable material produced as in Example 3 (PVA-3) is molded as a macroporous tissue scaffold. BMP-2 (bone morphogenetic protein-2) is contained in the cryogel. Prior to cryogelation, the polymer was autoclaved and sterilized. 9% by wt cryogel is used and the drug is incorporated as in Example 5.

Example 17

A biodegradable implantable material produced as in Example 3 (PVA-3) is molded as a firm cosmetic filler to be used as a butt implant. 9% by wt cryogel is used. A drug may be incorporated as in Example 5.

Example 18

The material from Example 2 (PVA-2) is loaded with isosorbide dinitrate for buccal drug delivery. 5% by wt cryogel containing the drug is prepared and molded in thin slabs, which are then dried to a constant mass. The film is intended to be used as a mucoadhesive buccal drug delivery vehicle.

Example 19

The material from Example 2 (PVA-2) is loaded with 5-aminosalicylic acid (mesalazine) intended to be used as an injectable for treatment of ulcerative colitis. 3% by wt cryogel is used. The drug is incorporated as in Example 5.

Example 20

The material from Example 2 (PVA-2) is loaded with fentanyl citrate intended for use in soft capsules for sustained release and chronic pain relief. 5% by wt cryogel is used. The drug is incorporated as in Example 5.

The specific examples and embodiments described herein are exemplary only in nature and are not intended to be limiting of the invention defined by the claims. Further embodiments and examples, and advantages thereof, will be apparent to one of ordinary skill in the art in view of this specification and are within the scope of the claimed invention.

What is claimed is:

1. A cryogel-forming vinyl alcohol co-polymer that forms a cryogel in an aqueous solution at a concentration of less than about 10% by weight, in the absence of a chemical cross-linking agent and in the absence of an emulsifier,
said vinyl alcohol co-polymer comprising a saponified product of a vinyl acetate co-polymer formed from at least about 80% by weight of vinyl acetate monomer, and at least about 3% by weight of acrylamide monomer or a mixture of acrylamide monomer and acrylic acid monomer.

2. The vinyl alcohol co-polymer of claim 1 operable to form a cryogel in an aqueous solution at a concentration of about 5% by weight or less, in the absence of a chemical cross-linking agent and in the absence of an emulsifier.

3. The vinyl alcohol co-polymer of claim 1, wherein the saponified product has a degree of saponification of at least about 90%.

4. The vinyl alcohol co-polymer of claim 1, comprising the saponified product of a vinyl acetate co-polymer formed from at least about 85% by weight of vinyl acetate monomer.

5. The vinyl alcohol co-polymer of claim 1, wherein the vinyl alcohol co-polymer is in the form of a powder.

6. A method of forming vinyl acetate co-polymer, comprising copolymerizing at least about 80% by weight of vinyl acetate monomer, and at least about 3% by weight of acrylamide monomer or a mixture of acrylamide monomer and acrylic acid monomer and optionally, at least about 5% by weight acrylic acid monomer, based on the weight of the monomers, in an aqueous medium with a polymerization initiator and a buffer, wherein the aqueous medium is free of emulsifier.

7. The method of claim 6, wherein at least about 85% by weight of the vinyl acetate monomer is employed in the copolymerization.

8. The method of claim 6 further comprising the step of:
saponifying the vinyl acetate co-polymer to form the cryogel-forming vinyl alcohol co-polymer.

9. The method of claim 8, wherein the vinyl acetate co-polymer is saponified to have a degree of saponification of at least about 90%.

10. The method of claim 8, wherein the vinyl alcohol co-polymer is precipitated in powder form.

11. A method of forming a vinyl alcohol co-polymer cryogel, comprising freezing an aqueous solution of the vinyl alcohol co-polymer of claim 1 at a temperature of from 0° C. to about −196° C. to form a molded mass, and thawing the molded mass to form a hydrogel.

12. The method of claim 7, further comprising the steps of:
freezing an aqueous solution of the vinyl alcohol co-polymer at a temperature of from 0° C. to about −196° C. to form a molded mass; and
thawing the molded mass to form a hydrogel.

13. The method of claim 12, wherein the aqueous solution of the vinyl alcohol co-polymer is frozen at a temperature of from about −15° C. to about −35° C.

14. The method of claim 12, wherein the aqueous solution comprises from about 1 to about 10% by weight of the vinyl alcohol co-polymer.

15. The method of claim 12, wherein the aqueous solution comprises from about 1 to about 5% by weigh of the vinyl alcohol co-polymer.

16. The method of claim 11 further comprising the step of:
freeze-drying the vinyl alcohol co-polymer cryogel formed, wherein a porous solid material is formed.

17. A vinyl alcohol co-polymer cryogel, comprising at least about 75% by weight water and formed from a vinyl alcohol co-polymer according to claim 1.

18. The cryogel of claim 17, comprising at least 90% by weight water.

19. The cryogel of claim 17, comprising at least 95% by weight water.

20. The cryogel of claim 17, wherein the cryogel is free of emulsifier and chemical cross-linking agents.

21. The cryogel of claim 17, wherein the cryogel is loaded with a therapeutic agent and/or a cosmetic agent.

22. The cryogel of claim 21, wherein the cryogel is loaded with at least one therapeutic agent comprising an analgesic, anesthetic, antibacterial, antifungal, anti-inflammatory, anti-itch, anti-allergic, anti-mimetic, immunomodulator, ataractic, sleeping aid, anxiolytic, vasodilator, bone growth enhancer, osteoclast inhibitor, or vitamin.

23. The cryogel of claim 17, wherein the cryogel is loaded with at least one functional agent comprising a colorant, taste enhancer, preservative, antioxidant, lubricant, rheology modulator, or thiolated mucoadhesive enhancer.

24. The cryogel of claim 23, wherein the cryogel is loaded with cysteine.

25. The cryogel of claim 17, wherein the cryogel is biodegradable.

26. The cryogel of any claim 17, wherein the cryogel is non-biodegradable.

27. The biomedical implant formed of the polyvinyl cryogel of claim 17.

28. The biomedical implant of claim 27, wherein the cryogel is loaded with at least one amino acid.

29. The biomedical implant of claim 27, wherein the cryogel is loaded with a biological macrocomplex.

30. The biomedical implant of claim 29, wherein the biological macrocomplex is a plasmid, virus, bacteriophage, protein micelle, or cell component organelle.

31. A thin film formed of the cryogel of claim 17.

32. The thin film of claim 31, wherein the cryogel is loaded with at least one thiolated mucoadhesion enhancer.

33. The cryogel of claim 1, wherein the acrylamide monomer does not exceed about 20% by weight.

34. The cryogel of claim 21, which is a drug-containing topical formulation for the treatment of wounds or burns.

35. The cryogel of claim 21, which is a topical formulation further comprising an antibiotic, an antiseptic or an antifungal drug.

36. The cryogel of claim 21, which is a topical formulation further comprising one or more drug selected from the group nitrofurazone, fusidic acid, mafenide, iodine, bacitracin, lidocaine, bupivacaine, levobupivacaine, prilocaine, ropivacaine, mepivacaine and aloe vera.

37. The cryogel of claim 21, which is a topical formulation further comprising iodine for the treatment of wounds or burns.

* * * * *